United States Patent [19]

Hughes

[11] Patent Number: 5,684,854
[45] Date of Patent: Nov. 4, 1997

[54] METHOD AND SYSTEM FOR DYNAMICALLY ESTABLISHING FIELD SIZE COINCIDENCE

[75] Inventor: John H. Hughes, Martinez, Calif.

[73] Assignee: Siemens Medical System Inc, Iselin, N.J.

[21] Appl. No.: 695,457

[22] Filed: Aug. 12, 1996

[51] Int. Cl.⁶ ........................................... A61B 6/08
[52] U.S. Cl. ..................... 378/206; 378/157; 378/207
[58] Field of Search .......................... 378/145, 146, 378/150, 151, 152, 153, 205, 206, 207

[56] References Cited

U.S. PATENT DOCUMENTS

| | | | |
|---|---|---|---|
| 3,921,001 | 11/1975 | Edholm et al. | 378/206 |
| 3,947,689 | 3/1976 | Wagner | 378/206 X |
| 5,446,548 | 8/1995 | Gerig et al. | 356/375 |
| 5,563,924 | 10/1996 | Winkelmann | 378/206 X |

Primary Examiner—David P. Porta
Attorney, Agent, or Firm—Heather S. Vance

[57] ABSTRACT

A method of establishing coincidence between a field size of a light field used in a setup mode of a radiation system and a field size of a radiation field used in an operation mode of the system includes providing automatic adjustment of field-defining structure to compensate for differences in optical properties of the light and the radiation. A light beam passing through the field-defining structure typically exhibits greater scattering than an X-ray beam passing through the structure. For each of a number of different settings of the field-defining structure, the difference between the field sizes of the light and the radiation are determined and recorded. Then, for a particular desired field size, the field-defining structure can be automatically adjusted to provide compensation. In the preferred embodiment, the field-defining structure includes jaws of a collimator of a radiation system and the determination of field size differences of the light and the radiation occurs for each of various energy level settings of the radiation system.

17 Claims, 4 Drawing Sheets

| | 6 MV | | | |
|---|---|---|---|---|
| SETTING | 5CM | 10CM | 20CM | 40CM |
| X-RAY | 5 | 10 | 20 | 40 |
| DISPLAY VALUE | 5 | 10 | 20 | 40 |
| LIGHT | 4.5 | 9.8 | 20 | 38 |
| DELTA | 0.5 | 0.2 | 0 | 2 |

METHOD AND SYSTEM FOR DYNAMICALLY ESTABLISHING FIELD SIZE COINCIDENCE

BACKGROUND OF THE INVENTION

The invention relates generally to a method to improve the setup of a treatment field for radiation treatment, and relates more particularly to establishing a field-size coincidence between a setup-mode light field, a treatment-mode radiation field, and a display that is used to facilitate the setup of the treatment field.

DESCRIPTION OF THE RELATED ART

Radiation-emitting devices are generally known and used, for instance, as radiation therapy devices for the treatment of patients. A radiation therapy device usually comprises a gantry which can be swiveled around a horizontal axis of rotation in the course of a therapeutic treatment. A linear accelerator is located in the gantry for generating a high-energy radiation beam for therapy. This high energy radiation beam can be an electron radiation or photon (X-ray) beam. During treatment, this radiation beam is trained on a zone of a patient lying in the isocenter of the gantry rotation.

To control the radiation emitted toward an object, a beam-shielding device such as a plate arrangement and/or collimator is usually provided in the trajectory of the radiation beam between the radiation source and the object. This beam-shielding device defines a field on the object to which a prescribed amount of radiation is to be delivered.

The radiation delivered to an object may be analyzed into primary and scattered components. The primary radiation is made up of the initial or original photons emitted from the radiation source, and the scattered radiation is the result of the photons scattered by the plate arrangement. The beam's radiation output in free space increases because of the increased plate-collimator scatter, which is added to the primary beam. In other words, a point in the field is subject not only to direct radiation (which is the primary component), but also to radiation that is scattered from the plate arrangement. The ratio of the radiation output in air with the scatterer to the radiation output without the scatterer for a reference field (for instance 10×10 cm) is commonly called the "output factor" or the "collimator scatter factor." The concept and definition of the output factor are well understood in the art.

Thus, due to these scattered photons, the dose rate applied to the surface of the object changes dependent on the size of the opening in the plate arrangement, that is, on the field size. This means that the radiation emitted to the same spot, for instance in the center of the radiation beam onto the object, changes according to the size of the opening in the plate arrangement. When the plate arrangement shows only a small opening, then the accumulated dose at the same spot is less than the accumulated dose at the same spot when the opening is big.

The field size of a radiation therapy device is important, since it determines the region of the patient that will be exposed to the radiation. In the setup mode of operation of the device, a source of visible light may be activated to project a light field onto the patient from the treatment head. The light field facilitates the adjustment of beam parameters and the proper positioning of the patient relative to the treatment head.

The field size is adjusted by varying an aperture through a collimator in the treatment head. The aperture is defined by settings of X-axis collimator jaws and Y-axis collimator jaws. The jaws are blocks of radiation-attenuating material that determine the field size by limiting the angular spread of the beam. By convention, the X-axis jaws are located below the Y-axis jaws.

Ideally, the field size of an X-ray radiation beam is a duplicate of the field size of the light that is used in the setup for the patient. However, there are factors that make it difficult to achieve the radiation field size-to-light-field size coincidence. The characteristics (light intensity, spot size, and position) of the visible light beam and the X-ray beam are significantly different. Moreover, different X-ray energies have different scattering components, another phenomenon that renders field size coincidence difficult. The penumbra of the two field edges will be dissimilar. As a consequence, if the collimator jaws are adjusted during a setup procedure so as to illuminate only the area to be treated, the field size of the X-ray beam may be significantly different.

In order to increase the coincidence between the light field size and the radiation field size, trimmers may be attached to the edges of the jaws. The trimmers are formed of a material that is transparent to the X-ray radiation but that blocks the visible light. For example, the trimmers may be formed of aluminum. Generally, the light field is greater than the X-ray field, so that trimmers of the appropriate width will at least decrease the difference. The trimmers may be X-ray transparent blades that project slightly (e.g., 4.3 mm) beyond the faces of collimator jaws to trim the light field. However, the phenomena that create the non-coincidence are partially dependent upon energy levels. Trimmers that are suitable when the radiation system is set to provide radiation at a relatively low energy level (e.g., 6 MV) will be less effective in establishing coincidence if the system is reset to provide radiation at a higher energy level (e.g., 23 MV). Optionally, the width of the trimmers may be selected to achieve field size-to-field size coincidence at the center of the range of energy levels that can be generated by the system, but this requires a user to concede to non-optimum conditions at the high and low ends of the energy capabilities of the system.

What is needed is a method and system that dynamically establish coincidence between field sizes of a light field in a setup mode and a radiation field in an operation mode of a radiation system, regardless of radiation energy levels.

SUMMARY OF THE INVENTION

Field size coincidence for a radiation system is provided by automatically adjusting field-defining structure each time that the system is switched between a light-emitting mode and a radiation-emitting mode. In one embodiment, the field-defining structure is a jaw assembly of a collimator of an X-ray system in which the light-emitting mode is used in a setup procedure for applying radiation to a preselected area. The automatic adjustment of the field-defining structure is implemented to compensate for a dimensional difference between a light field that is defined in the light-emitting mode and a radiation field that is defined in the radiation-emitting mode. The required compensation is dependent upon at least one variable, such as the dimensions of the area that is to be radiated and the energy level of the radiation. Therefore, the preferred embodiment includes determining and storing data that is indicative of desired increments of compensation at various settings of the field-defining structure and at various energy levels of radiation.

DETAILED DESCRIPTION

Figure 1:
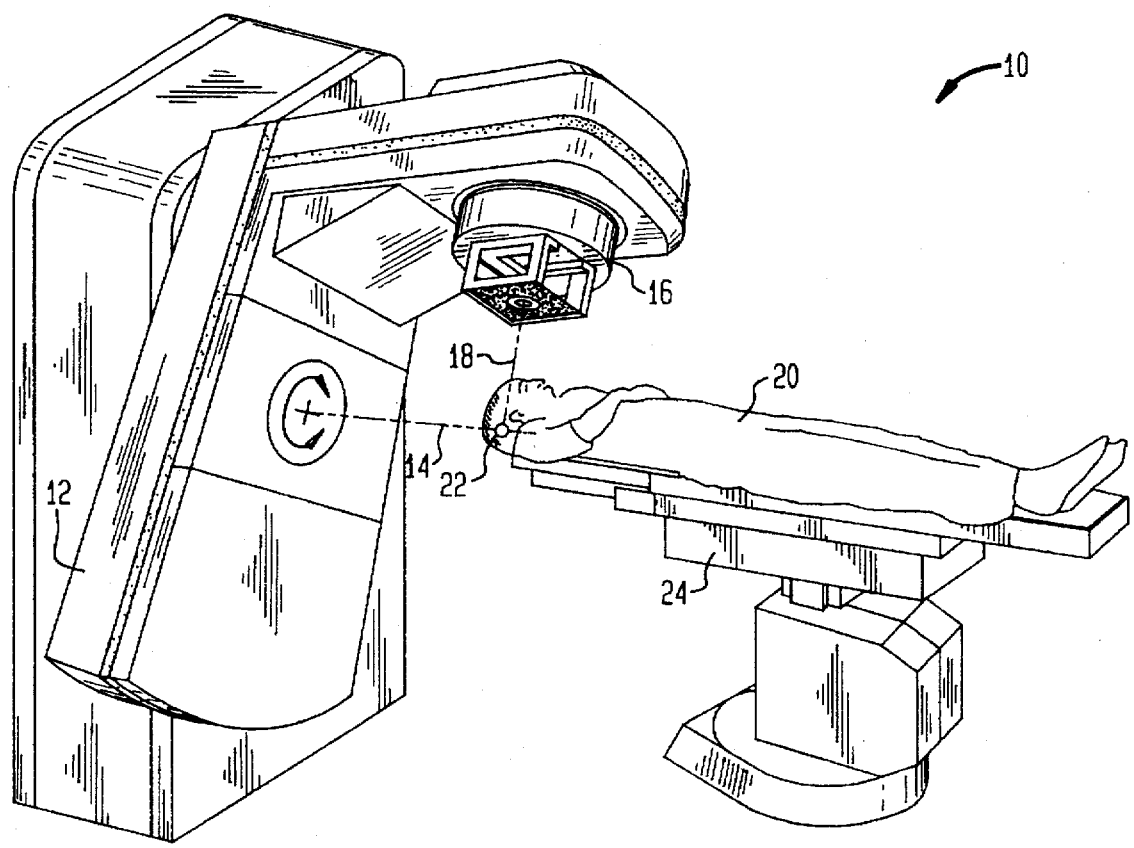
FIG. 1 is a perspective view of a radiation system for providing automated field size coincidence in accordance with the invention.

With reference to FIG. 1, a radiation system 10 for medical applications is shown as including a gantry which can be swiveled around a horizontal axis of rotation 14 in the course of a therapeutic treatment. A treatment head 16 of the gantry directs a radiation beam along axis 18 toward a patient 20. The radiation beam is generated by a linear accelerator within the gantry. The radiation beam may be electron radiation or photon radiation, i.e., X-ray radiation. The radiation beam is trained on a treatment zone 22 of the patient.

The treatment parameters of a particular therapeutic session are defined when the radiation system 10 is in a setup mode. The treatment zone 22 is properly positioned relative to the gantry 12 by rotating the gantry about the horizontal axis 14 and by moving a treatment table 24 on which the patient 20 rests. After the treatment zone has been properly positioned, beam parameters are set. Preferably, the radiation system 10 allows a selection of energy levels, such as X-ray energy levels of 6 MV, 15 MV and 23 MV. The dimensions of the radiation field should match the dimensions of the treatment zone 22, so that only that region of the patient that is to be treated will be exposed to radiation. As will be explained more fully below, the dimensions of the radiation field are determined by field-defining structure within the treatment head 16. During the setup stage, the beam that is projected along axis 18 is a beam of visible light that allows a user to non-intrusively adjust the aim and the dimensions of the beam that is projected along the axis 18. A projection lamp may be activated during the setup mode of the system to provide the desired light field at the treatment zone 22. When the system is switched to the operation mode, the visible light is replaced with the radiation beam.

A concern in the use of the visible light beam to set up the dimensions of the subsequently used radiation beam is that the effects of scattering and diffraction are partially dependent upon frequency and energy level. Consequently, there is often a difference in the field size of the light beam during the setup mode and the field size of the radiation beam during the operation mode of the radiation system 10. Typically, the field size of the light field is greater than the field size of the radiation field. Trimmers may be used to reduce the light field size without affecting the radiation field size, but unless the trimmers are changed with almost each change in the desired treatment beam parameters, a substantially exact coincidence between the two field sizes is not possible. Therefore, the invention provides a dynamic adjustment to compensate for the dimensional differences between the field sizes.

Figure 2:
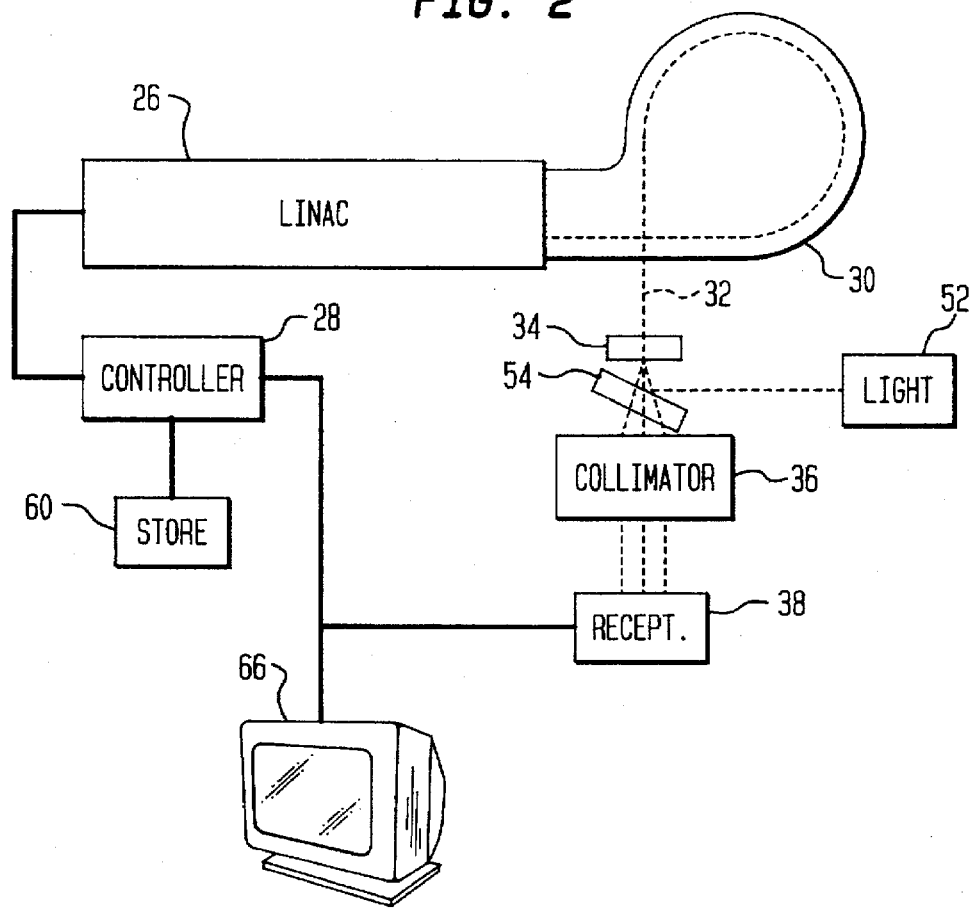
FIG. 2 is a block diagram of the radiation system of FIG. 1.

Referring now to FIG. 2, a conventional linear accelerator ("linac") 26 may be used to generate the electron beam that is emitted from the radiation system 10 of FIG. 1. The energy level of the electron beam is determined by a controller 28 that activates an electron gun of the linac. The electrons from the electron gun are accelerated along a waveguide using known energy-transfer techniques.

The electron beam from the waveguide of the linac 26 enters a conventional guide magnet 30, which bends the electron beam by approximately 270°. The electron beam then exits through a window that is transparent to the beam, but preserves the vacuum condition within the linac.

Along the axis 32 of the electron beam is a scattering foil or a target 34. If the element 34 is a scattering foil, the electrons are spread to form a conical beam. On the other hand, if the element 34 is a target, the radiation beam is an X-ray beam.

A collimator 36 is positioned along the radiation beam path. The collimator functions to limit the angular spread of the radiation beam. For example, blocks of radiation-attenuating material may be used to define a radiation field that passes through the collimator to a receptor 38. The receptor may be the patient, or may be structure that is used to calibrate the radiation system during the calibration process that will be described below.

Figure 3:
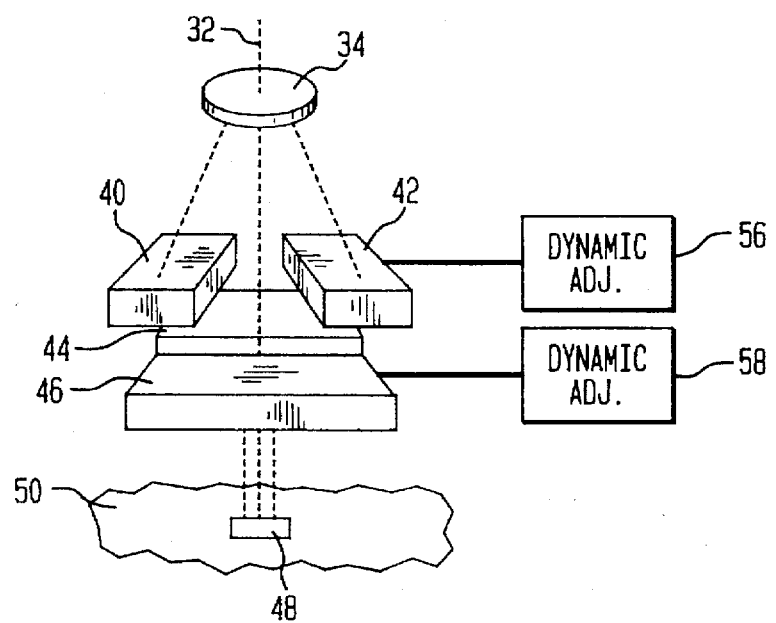
FIG. 3 is a schematical representation of field-defining structure for the collimator of FIG. 2.

In one embodiment, the collimator 36 includes Y-axis jaws and X-axis jaws. In FIG. 3, Y-axis jaws are represented by first and second blocks 40 and 42 of radiation-attenuating material. Below the Y-axis jaws are the third and fourth blocks 44 and 46 that form the X-axis jaws. The spacing between the first and second blocks defines one dimension of the target zone 48 on a body 50, while the spacing between the third and fourth blocks defines the perpendicular dimension. As used with regard to the invention, "field-defining structure" refers to devices such as those shown in FIG. 3 for determining the dimensions of the target zone 48.

SOFTWARE SOLUTION TO COINCIDENCE PROBLEM

In the setup stage of the radiation system, the linac 26 is deactivated and a light source 52 is energized. The light source directs visible light to an optical element, such as a beam splitter, for redirecting the light into the collimator 36. The light source may be a 150 W quartz halogen lamp, but this is not critical. The optical element 54 should be transparent to radiation from the linac 26. When the light has passed through the collimator, the beam can be used to properly position the jaws of the collimator. For example, if the target zone 48 on the body 50 of FIG. 3 is a tattooed area on a patient, the blocks 40–46 may be adjusted until the light field that is emitted from the collimator coincides with the area of the target zone. The radiation system can then be switched to an operation mode in which the radiation beam takes the place of the light beam. However, unlike prior art radiation systems, dynamic adjusters 56 and 58 automatically vary the settings of the X-axis jaws and the Y-axis jaws in order to compensate for any inherent dissimilarities between field sizes of the light beam and the radiation beam. Adjustment of X-axis and Y-axis jaws could also take place when the light is turned on.

The dynamic adjusters 56 and 58 are controlled by the controller 28. In the preferred embodiment, the increments of adjustment are calculated according to tables stored at element 60 in FIG. 2. Thus, the "trimming" of the light field is enabled by computer software. For a given energy level of X-ray radiation and for a desired field dimension of 10 cm, it may be known from data stored at component 60 that for the appropriate setting of the jaws for the light field there will be a difference of 0.2 cm when the radiation beam is activated during the operation mode. The dynamic adjusters will automatically vary the blocks 40–46 to compensate for the difference.

The structure for forming the dynamic adjusters 56 and 58 is not critical to the invention. Any device that can be electronically controlled to manipulate the settings of the blocks 40-46 may be utilized.

Figure 4:
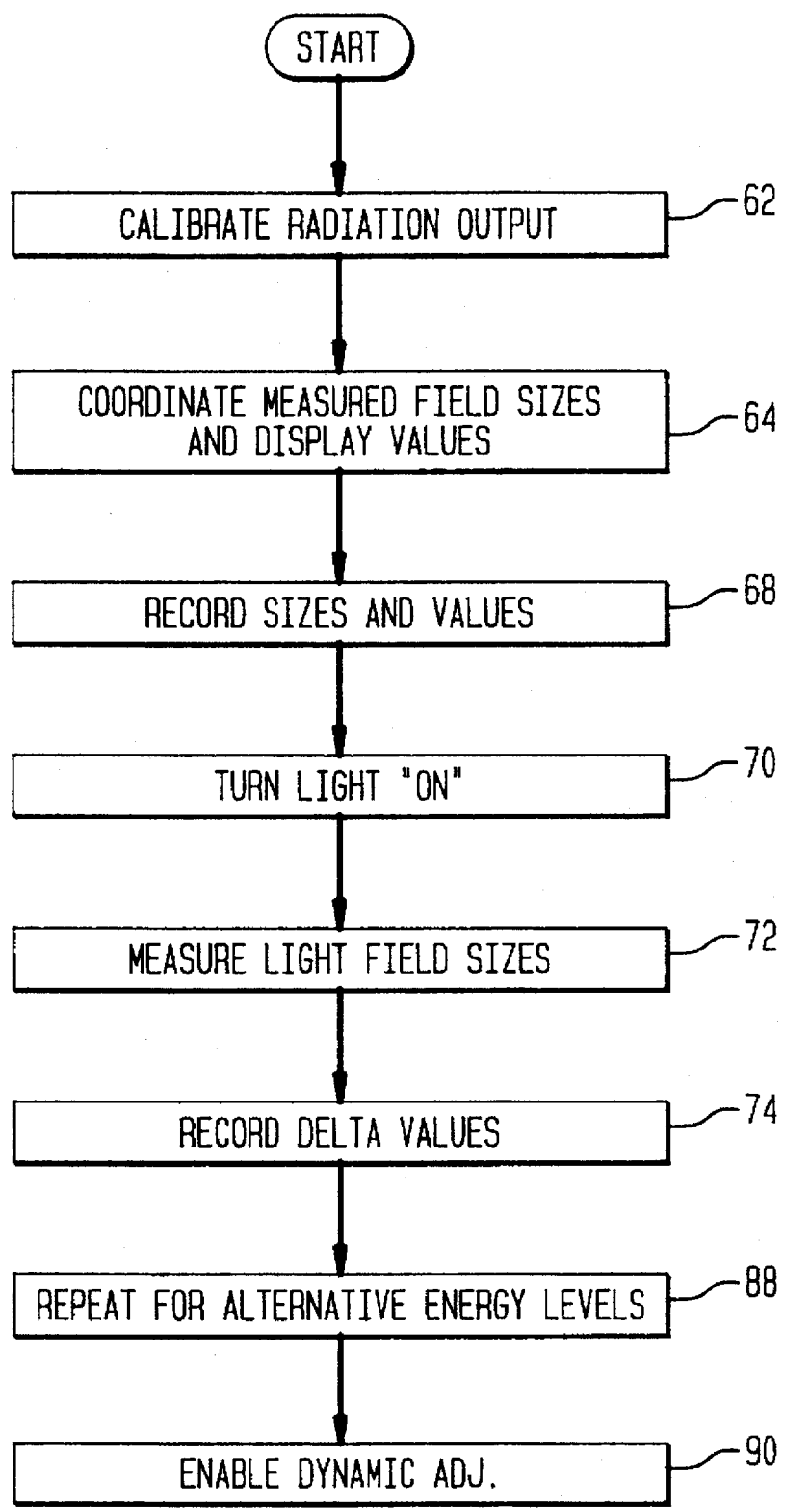
FIG. 4 illustrates one embodiment of a process flow for implementing automated field size coincidence in accordance with the invention.

FIG. 4 illustrates one embodiment of a process for establishing coincidence between field sizes of a light field and a radiation field for the system 10 of FIG. 1. In step 62, the collimator field size is calibrated for the radiation output. Calibration of a radiation system for X-ray output is well known in the art, and any of the known techniques may be utilized in executing step 62. For example, a tank of water may be used to simulate a human body or other object and a probe may be used to measure radiation through the water. With the water surface at a 900 mm target-surface distance (TSD) and the probe at isocenter, the field size may be measured for a particular setting of the jaws. Conventionally, the field size measurement with regard to the fifty percent maximum dose value of the radiation. This measurement is stored at element 60 of FIG. 2. The procedure is repeated for a number of settings of the jaws, and each measurement is recorded. Preferably, the energy level of the radiation and the TSD are constant throughout the calibration step, since these two factors affect scattering and diffraction of the beam. However, as will be explained more fully below, the process steps preferably are carried out with regard to more than one energy level and/or with regard to more than one TSD.

In step 64, the measurements of field sizes acquired during step 62 are coordinated with values on a display that is employed by a user of the radiation system. A display monitor 66 is shown in FIG. 2. The monitor will include designations of dimensions. In the exemplary embodiment of FIG. 4, the indications are manipulable, so that the display values can be coordinated with the measured field sizes at each of the various settings of the jaws. In step 68, the data from steps 62 and 64 are recorded.

Figures 5, 6:
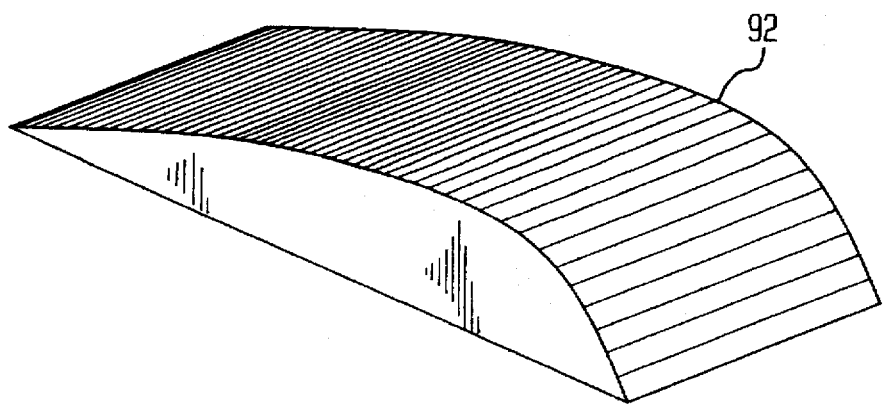
FIG. 5 is a table of field sizes that are calculated and stored during implementation of the process of FIG. 4.
FIG. 6 illustrates an acceptable shape for a mirror in accordance with the invention.

The light 52 of FIG. 2 is then turned "on," as shown in step 70 of FIG. 4. For the same jaw settings that were used in the calibration of the radiation output at step 62, the light field sizes are measured in step 72. This may be done using conventional techniques. For example, the tank of water used in step 62 may be replaced with graph paper or with a film pack. The portion of the graph paper or film that is illuminated by the light beam is measured for each setting. Next, the dimensional difference between the light field and the radiation field is determined for each jaw setting. The delta values are recorded at step 74. In one embodiment, a delta value is merely a difference between the measured light field size from step 72 and the display monitor value for the particular setting of the jaws. Because the phenomena of scattering and diffraction will have different effects upon the X-ray beam and light beam, the delta values will at least partially be indications of the different effects. Following step 74, a table may be formed from the data stored at component 60 of FIG. 2. Such a table 76 is shown in FIG. 5.

Within table 76, the first row indicates the various settings of the jaws that affect the field size of concern. That is, the first row is an indication of the setting 78 of the field-defining structure that can be dynamically adjusted. The second row 80 shows the measured field sizes for the X-ray field at an energy level of 6 MV. The values of rows 78 and 80 are identical, since the radiation output was calibrated at step 62.

In the third row 82, the display values of the monitor 66 have been recorded. Since the X-ray field sizes and the display values were coordinated at step 64 of FIG. 4, the values of row 82 are identical to the values of row 80. With the X-ray output turned "off" and the light 52 turned "on," the light field sizes were measured at step 72 and recorded in the fourth row 84 of table 76. The final row 86 records the delta values that are the dimensional differences between the X-ray field size of row 80 and the light field size of row 84.

In step 88 of FIG. 4, the steps for generating the table 76 may be repeated for alternative energy levels of the radiation system. Since the radiation field sizes may vary depending upon the energy level of the radiation beam, there are potentially different delta values for the different energies. By generating separate tables that are implemented based upon the setting of energy levels, the dynamic compensation process is not a process that requires significant compromise, as would be the case if aluminum micro-trimmers were used to achieve field size coincidence.

The dynamic adjusters 56 and 58 are enabled at step 90 of the process of FIG. 4. Then, in the operation of the radiation system 10 of FIGS. 1-3, a user selects a setting for the field-defining structure (i.e., the blocks 40-46) in the conventional manner of forming a light field that corresponds to the target zone of the patient 20. This target zone may be delineated by a tattoo on the patient 20, but this is not critical. The light field is provided by activating a light source 52 to pass light through the collimator 36. The adjustment of the field-defining structure is accomplished during the setup mode of the radiation system.

Once the blocks 40-46 have been properly set with respect to the dimensions of the light field, the system may be switched to the operation mode. The controller 28 may provide the switching capability. As the switching function is executed, the dynamic adjusters 56 and 58 are varied by an increment defined by the appropriate delta value in row 86 of FIG. 5. For example, if the light field that was established during the setup mode had a field size that spaced the first block 40 away from the second block 42 by a distance of 4.5 cm, the dynamic adjustment will be an incremental increase of 0.5 cm. This spaces the blocks apart by a distance of 5 cm. The incremental adjustment is performed in software, so that the user is not required to provide further adjustments. Based upon the data of table 76, the controller 28 is able to interpolate and/or extrapolate the information in order to provide the appropriate compensation for a setting that is not contained within stored memory.

While the preferred embodiment of FIG. 4 uses the X-ray output to calibrate the system in steps 62 and 64, there may be some applications in which the light field is used in the calibration process. The invention may be used in applications outside of the medical environment.

OPTICAL SOLUTIONS TO THE COINCIDENCE PROBLEM

In addition to the use of computer software to provide field size coincidence, there are optical solutions. One such solution is to provide a curved mirror to compensate for the dimensional error between the light field size and the radiation field size. It has been determined that an asymmetrically shaped mirror provides the better results. Specifically, a parabolic mirror is preferred. The equation for the mirror surface and the positioning of the mirror relative to a target area has the form:

$$f(x) = Ax^2 + Bx + C$$

wherein the coefficient "A" describes the curvature of the mirror, "B" is a tilt term, and "C" is an offset term that by convention determines a vertical position. When the term "A" is 0, the mirror is flat, while a negative value describes a convex surface.

It has been determined that the mirror should be asymmetrical, because the intersection of the light with the mirror for a given field size is not equally spaced from the collimator axis when comparing opposite jaws. Therefore, one side of the mirror has a greater curvature. An acceptable shape of a mirror 92 is shown in FIG. 6, but the curvature is exaggerated for purposes of illustration. Actual curvature is more likely to be a subtle curvature of approximately 0.002 to 0.003 inches per inch.

One difficulty with this mirror solution is that while it works well with positive field sizes, the use of the curved mirror increases the error if one of the collimator jaws defines a negative field size, i.e., both of the blocks of the jaw are on the same side of a midline. Another problem is that the mirror does not rotate with the collimator, so that this approach to correcting the light penumbra only works with the collimator at 0 degrees. When the collimator is at 90 degrees, there is no correction. It may be feasible to provide a three-dimensional shape that would be adequate, but this may not be cost efficient.

Another possible solution is to provide a more compact light source and a second mirror, with the second mirror being placed in the head area of the radiation system. By adding an elliptical reflector behind a conventional light source that produces approximately 20 lux at isocenter, the illuminance may increase to 100 lux. This increase in illuminance reduces the perceived light field penumbra without an increase in the cost of the light source. However, the uniformity at the edges of the light field is obtained at the cost of creating a dark spot at the beam axis, since the lamp blocks some of the light reflected by the elliptical reflector. It may be possible to use frosted glass or some other method to diffuse the light, but the diffusion reduces the efficiency.

Alternate light sources provide some benefits. For example, an arc lamp may be used in place of the conventional tungsten-filament, halogen-filled, quartz lamp. The arc lamp provides a significantly greater illuminance. When focused on a small aperture, no field size compensation was required. However, the arc lamp is an expensive alternative and because of size and safety reasons, the best location for the lamp and power supply would be in the machine stationary structure, so that light guidance (e.g., a fiber optic bundle) may be required.

Another alternative light source is a laser. The laser provides the advantage of producing a small and well-collimated beam. The beam could be focused by a converging lens through a very small aperture to produce little or no penumbra. To achieve a 40 lux, 50 cm diameter field, however, would require 8 lumens of luminous power. At the wavelength of a typical HeNe laser, one watt of power is approximately equal to 250 lumens. Consequently, a very powerful and perhaps prohibitively expensive 32 mW laser would be required.

As previously noted, fiber optics may be utilized. Because there is limited space within the head area of the radiation device, the application of fiber optics is attractive. The challenge with this approach is keeping the efficiency sufficiently high to provide at least equal illumination that at least equals that of the existing system.

A final approach is to provide a light source on the target slide of the radiation device. The advantage of this approach is that the use of a mirror would not be required and the alignment procedure would be simplified. The space that the mirror occupies on conventional radiation devices could be used for shielding material, automated wedges, or the like. To implement this approach, the light source would occupy a new position on the target slide, and the target slide would move between a patient setup position and an actual treatment position. The conventional thickness of the target slide presents difficulties in placing the light source directly on the slide, so that there may be a need to increase the structural integrity of the target slide or to provide a remote light source that is optically coupled to a fiber optic bundle.

I claim:

1. A method of establishing coincidence between a dimension of a light field used in a setup mode and a corresponding dimension of a radiation field used in an operation mode of a radiation system having field-defining structure that determines said dimensions, said method comprising steps of:

determining a dimensional difference between said light field and said radiation field at each of a plurality of settings of said field-defining structure; and when switching between said setup mode and said operation mode of said radiation system, automatically adjusting said field-defining structure to compensate for said dimensional difference.

2. The method of claim 1 wherein said step of determining a dimensional difference between said light field and said radiation field includes calibrating said radiation field at said plurality of settings of said field-defining structure and further includes comparing said light field to results of calibrating said radiation field.

3. The method of claim 2 wherein said step of calibrating said radiation field includes, at each of said settings, adjusting a displayed value of said field size of said radiation field to correspond to a measured value of said field size of said radiation field.

4. The method of claim 3 wherein said step of comparing said light field to said results of calibrating includes, at each of said settings, determining a difference between said displayed value of said field size and a measured value of said field size of said light field, thereby providing a basis for determining said difference between said light field and said radiation field for each of said settings of said field-defining structure.

5. The method of claim 1 wherein said step of automatically adjusting said field-defining structure includes varying jaws of a collimator that is connected to a linear accelerator.

6. The method of claim 1 wherein said step of determining said dimensional difference at said settings includes forming and storing a table of delta values such that each setting of said field-defining structure is associated with a delta value indicative of a difference in measured field sizes of said radiation field and said light field at said each setting.

7. The method of claim 6 wherein said step of automatically adjusting said field-defining structure when switching between said setup and operation modes is a step that is responsive to a delta value stored at said table.

8. The method of claim 6 wherein said step of automatically adjusting said field-defining structure includes interpolating an unknown delta value based upon known delta values stored at said table.

9. The method of claim 1 further comprising steps of changing an energy level of radiation that defines said radiation field and then determining a second set of dimensional differences for which said field-defining structure is to be automatically adjusted to provide compensation.

10. A method of establishing coincidence of a light field and a radiation field emitted from an X-ray collimator comprising steps of:

(a) adjusting jaws of said collimator to provide a first setting of said jaws;

(b) separately directing X-ray radiation and visible light through said jaws;

(c) storing data indicative of a difference between sizes of a radiation field and a light field formed when respectively directing said X-ray radiation and said visible light through said jaws;

(d) changing settings of said jaws a plurality of times and repeating steps (b) and (c) for each setting, thereby forming a first set of data indicative of differences of said sizes; and (e) based upon generating a radiation field having a desired field size and, based upon said stored data, automatically adjusting said jaws to at least partially offset said difference between said sizes of said radiation and light fields.

11. The method of claim 10 wherein said step (c) of storing data includes:

(c.1) calibrating said size of said radiation field and a display value of said size of said radiation field; and (c.2) then comparing said display value to said size of said light field when said jaws are at said first setting.

12. The method of claim 10 wherein said steps (a), (b), (c) and (d) are repeated after said X-ray radiation is adjusted with respect to energy level such that a second set of data is stored for said adjusted energy level.

13. A system to establish coincidence of a light field and a radiation field emitted from an X-ray collimator comprising:

a first source of a beam of X-ray radiation;

a second source of visible light aligned to direct a beam of light along an axis that is generally coaxial with said beam of said X-ray radiation;

movable jaws positioned along said axes of said beams of light and X-ray radiation to define a light field and a radiation field, respectively;

control means, connected to said first and second sources, for selectively switching between activating said second source when said system is in a setup mode and activating said first source when said system is in an operation mode;

memory means for storing a table of data indicative of differences between sizes of said light field and said radiation field at a plurality of settings of said movable jaws; and automated means, responsive to said control means, for varying said movable jaws by an increment determined by said table of data when said control means switches between said setup mode and said operation mode.

14. The system of claim 13 further comprising a display screen having a display of said radiation field, said display screen having an indication of an anticipated size of said radiation field when said jaws are at a particular setting.

15. The system of claim 13 wherein said memory means has a plurality of stored tables of data indicative of differences between said sizes, with said each table being specific to a particular energy level of said beam of X-ray radiation.

16. The system of claim 13 wherein said movable jaws include X-axis jaws and Y-axis jaws that are adjustable to define radiation fields of selectable dimensions, said automated means being connected to incrementally change at least one of said X-axis and Y-axis jaws.

17. The system of claim 13 further comprising computing means for interpolating data indicative of said differences between said sizes when said movable jaws are at a setting that is different than said plurality of settings.

* * * * *